United States Patent
Hoon

(10) Patent No.: US 6,465,177 B1
(45) Date of Patent: Oct. 15, 2002

(54) DETECTION OF LOSS OF HETEROZYGOSITY IN TUMOR AND SERUM OF MELANOMA PATIENTS

(75) Inventor: Dave S. B. Hoon, Los Angeles, CA (US)

(73) Assignee: John Wayne Cancer Institute, Santa Monica, CA (US)

(*) Notice: Subject to any disclaimer, the term of this patent is extended or adjusted under 35 U.S.C. 154(b) by 0 days.

(21) Appl. No.: 09/179,704

(22) Filed: Oct. 26, 1998

(51) Int. Cl.[7] ............................ C12Q 1/68; C12P 19/34; C07H 21/04
(52) U.S. Cl. ...................... 435/6; 435/91.2; 536/23.1; 536/24.31; 536/24.33
(58) Field of Search ................... 435/6, 91.2; 536/23.1, 536/24.31, 24.33

(56) References Cited

FOREIGN PATENT DOCUMENTS

| WO | WO 94/19492 | | 9/1994 |
| WO | WO 97/15686 | | 5/1997 |
| WO | 98/08980 | * | 3/1998 |
| WO | WO 98/31324 | | 7/1998 |

OTHER PUBLICATIONS

Healy et al. Cancer Research. 56: 589–593, Feb. 1996.*
Sidransky. Science. 278: 1054–1058, Nov. 1997.*
Healy et al. Oncogene. 16: 2213–2218, Feb. 1996.*
Ankers, Philippe et al., "K–ras Mutations Are Found in DNA Extracted From the Plasma of Patients With Colorectal Cancer" *Gastroenterology* 112:1114–1120 (1997).
Baker, Suzanne J. et al., "Chromosome 17 Deletions and p53 Gene Mutations in Colorectal Carcinomas," *Science* 244:217–221 (1989).
Call, Katherine M. et al., "Isolation and Characterization of a Zinc Finger Polypeptide Gene at the Human Chromosome 11 Wilms' Tumor Locus" *Cell* 60:509–520 (1990).
Chen, Xu Qi et al., "Microsatellite Alternations in Plasma DNA of Small Cell Lung Cancer Patients" *Nature Medicine* 2:9:1033–1035 (1996).
Fearon, Eric R. et al., "A Genetic Model for Colorectal Tumorigenesis" *Cell* 61:759–767 (1990).
Friend, Stephen H. et al., "A human DNA Segment with Properties of the Gene That Predisposes to Retinoblastoma and Osteosarcoma" *Nature* 323:643–646 (1986).
Fujiwara, Yoshiyuki et al., "Plasma DNA Microsatellites as Tumor–Specific Markers and Indicators of Tumor Progression in Melanoma Patients," *Cancer Research* 59:1567–1571(1999).
Gyapay, Gabor et al., "The 1993–94 Genethon Human Genetic Linkage Map" *Nature Genetics* 7:246–339 (1994).
Hahn, Stephan A. et al., "DPC4, A Candidate Tumor Suppressor Gene at Human Chromosome 18q21.1" *Science* 271:350–353 (1996).
Herbst, Rudolf A. et al., "Loss of Heterozygosity for 10q22–10qter in Malignant Melanoma Progression," *Cancer Research* 54:3111–3114 (1994).
Hol, F.A. et al., "Improving the Polymorphism Content of the 3' UTR of the Human IGF2R Gene" *Human Molecular Genetics* 1:5–347 (1992).

(List continued on next page.)

*Primary Examiner*—Carla J. Myers
(74) *Attorney, Agent, or Firm*—Bingham McCutchen LLP

(57) ABSTRACT

A method is provided for assessing allelic losses on specific chromosomal regions in melanoma patents. The method relies on the evidence that free DNA may be released in the plasma/serum of cancer patients allowing the detection of DNA with LOH in the plasma/serum of cancer patients by analysis for microsatellite markers. The amount of and specific allelic loss allows a prognosis to be made regarding tumor diagnosis and progression, tumor metastasis, tumor recurrence, and mortality.

108 Claims, 3 Drawing Sheets

OTHER PUBLICATIONS

Figure 1:
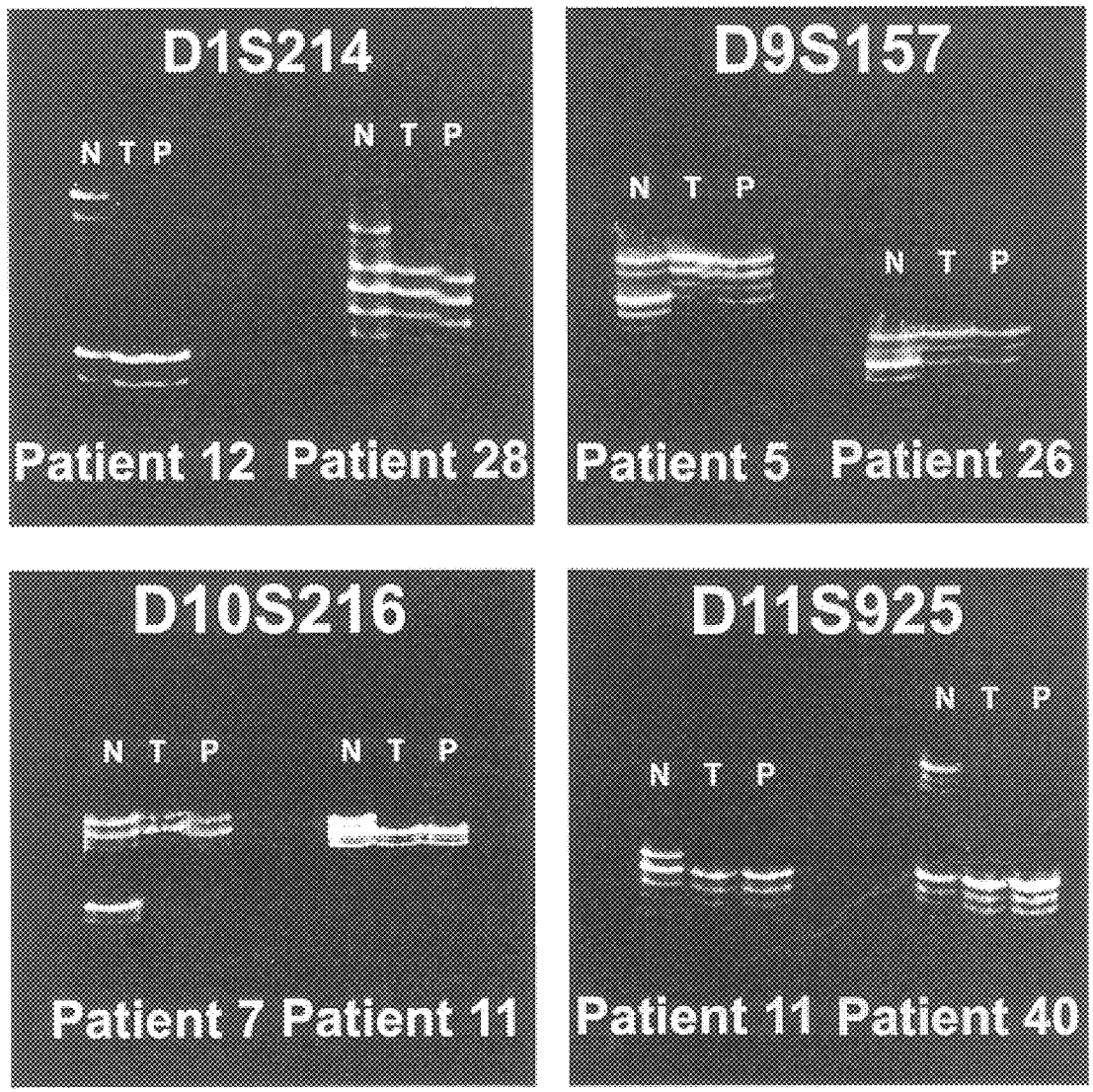

Isshiki, Koichi et al., "Chromosome 9 deletion in sporadic and familial melanomas in vivo," *Oncogene* 9:1649–1653 (1994).

Kamb, Alexander et al., "A Cell Cycle Regulator Potentially Involved in Genesis of Many Tumor Types" *Science* 264:436–440 (1994).

Kinzler, Kenneth W. et al., "Identification of FAP Locus Genes from Chromosome 5q21" *Science* 253:661–665 (1991).

Kuroki, Tamotsu et al., "Accumulation of Genetic Changes During Development and Progression of Hepatocellular Carcinoma: Loss of Heterozygosity on Chromosome Arm 1p Occurs at an Early Stage of Hepatocarcinogenesis" *Genes, Chromosomes & Cancer* 13:163–167 (1995).

Lasko D. et al., "Loss of Constitutional Heterozygosity in Human Cancer" *Annu. Rev. Genet.* 25:281–314 (1991).

Latif, Farida et al., "Identification of the von Hippel–Lindau Disease Tumor Suppressor Gene" *Science* 260:1317–1320 (1993).

Mao, Li et al., "Molecular Detection of Primary Bladder Cancer by Microsatellite Analysis" *Science* 271:659–662 (1996).

Minna et al., *Cancer Principals and Practices of Oncology*, DeVita et al., ed., Lippincott, Philadelphia 591–705 (1989).

Miozzo, Monica et al., Microsatellite Alterations in Bronchial and Sputum Specimens of Lung Cancer Patients Cancer Research 56:2285–2288 (1996).

Nawroz, Homaira et al., "Microsatellite Alterations in Serum DNA of Head and Neck Cancer Patients" *Nature Medicine* 2:9:1035–1037 (1996).

Puig, Susana et al., "Chromosome 9p Deletions in Cutaneous Malignant Melanoma Tumors: The Minimal Deleted Region Involves Markers Outside the p16 (CDKN2) Gene," *Am. J. Hum. Genet.* 57:395–402 (1995).

Rasio, Debora et al., "Loss of Heterozygosity at Chromosome 11 q in Lung Adenocarcinoma: Identification of Three Independent Regions," *Cancer Research* 55:3988–3991 (1995).

Rouleau, Guy A. et al., "Alteration in a New Gene Encoding a Putative Membrane–organizing Protein Causes Neuro–fibromatosis Type 2" *Nature* 363:515–521 (1993).

Sorenson George D. et al., "Soluble Normal and Mutated DNA Sequences from Single–Copy Genes in Human Blood" *Cancer Epidemiology, Biomarkers & Prevention* 3:67–71 (1994).

Steck, Peter A. et al., "Identification of a Candidate Tumor Suppressor Gene, *MMAC1*, at Chromosome 10q23.3 That is Mutated in Multiple Advanced Cancers" *Nature Genetics* 15:356–362 (1997).

Stroun, Maurice et al., "Isolation and Characterization of DNA From the Plasma of Cancer Patients" *Eur. J. Cancer Clin. Oncol.* 23:6:707–712 (1987).

Stroun M. et al., "Neoplastic Characteristics of DNA Found in the Plasma of Cancer Patients" *Oncology* 46:318–322 (1989).

Tsao, Hensin et al., "Identification of PTEN/MMAC1 alterations in uncultured melanomas and melanoma cell lines," *Oncogene* 16:3397–3402 (1998).

Vasioukhin, Valeri et al., "Point Mutations of the N–ras Gene in the Blood Plasma DNA of Patients With Myelodysplastic Syndrome or Acute Myelogenous Leukaemia" *British Journal of Haematology* 86:774–779 (1994).

Vogelstein, Bert et al., "Genetic Alterations During Colorectal–Tumor Development" *New England Journal of Medicine* 319:9:525–532 (1988).

* cited by examiner

Detailed Microsatellite Analysis of Advanced Melanoma with LOH in Plasma

| Patient ID | | D1S214 | D1S228 | D3S1293 | D6S264 | IGFIIR | D9S157 | D9S161 | D10S212 | D10S216 | D11S925 |
|---|---|---|---|---|---|---|---|---|---|---|---|
| 2  | T | ○ | ○ | ⊘ | ⊘ | ○ | ● | ● | ● | ⊘ | ⊘ |
|    | P | ○ | ○ | ⊘ | ⊘ | ○ | ○ | ● | ○ | ⊘ | ⊘ |
| 4  | T | ● | ⊘ | ⊘ | ● | ⊘ | ● | ● | - | ⊘ | ⊘ |
|    | P | ● | ⊘ | ⊘ | ● | ⊘ | ● | ● | - | ⊘ | ⊘ |
| 5  | T | ⊘ | - | - | ⊘ | ○ | ● | ○ | - | ⊘ | ⊘ |
|    | P | ⊘ | ○ | - | ⊘ | ○ | ● | ○ | - | ⊘ | ⊘ |
| 7  | T | ○ | ● | ○ | ○ | ⊘ | ○ | ○ | ⊘ | ● | ○ |
|    | P | ○ | ● | ○ | ○ | ⊘ | ○ | ○ | ⊘ | ● | ○ |
| 10 | T | ○ | ○ | - | ○ | ○ | ○ | ○ | ○ | ⊘ | ○ |
|    | P | ○ | ○ | - | ● | ○ | ○ | ○ | ○ | ⊘ | ○ |
| 11 | T | ● | ○ | ⊘ | ○ | ○ | ○ | ⊘ | ○ | ● | ● |
|    | P | - | - | ⊘ | ○ | ○ | ○ | ⊘ | ○ | ● | ● |
| 12 | T | ● | ● | ⊘ | ⊘ | ○ | ○ | ○ | ○ | ⊘ | - |
|    | P | ● | - | ⊘ | ⊘ | ○ | ○ | ○ | ○ | ⊘ | - |
| 13 | T | ⊘ | ⊘ | ● | ⊘ | ⊘ | ○ | ○ | ● | ⊘ | ⊘ |
|    | P | ⊘ | ⊘ | ● | ⊘ | ⊘ | ○ | ○ | - | ⊘ | ⊘ |
| 14 | T | - | - | - | ⊘ | ⊘ | ○ | ⊘ | ⊘ | ⊘ | ○ |
|    | P | ○ | ○ | ● | ⊘ | ⊘ | ○ | ⊘ | ⊘ | ⊘ | ○ |
| 18 | T | ⊘ | ○ | ⊘ | ⊘ | ⊘ | ○ | ● | - | ○ | ○ |
|    | P | ⊘ | ○ | ⊘ | ⊘ | ⊘ | ○ | ● | - | ○ | ○ |
| 21 | T | ● | ⊘ | ● | - | ○ | ● | ● | - | - | ○ |
|    | P | ○ | ⊘ | ● | - | ○ | ○ | ○ | - | - | ○ |
| 26 | T | ○ | ○ | ○ | ● | ○ | ● | ○ | ⊘ | ⊘ | ○ |
|    | P | ○ | ○ | ○ | ● | ○ | ● | ○ | ⊘ | ⊘ | ○ |
| 27 | T | ○ | ○ | - | - | ○ | - | ⊘ | - | ○ | ● |
|    | P | ● | ○ | - | - | ○ | - | ⊘ | - | ○ | ○ |
| 28 | T | ● | - | - | ⊘ | ⊘ | - | - | ⊘ | - | - |
|    | P | ● | ○ | ○ | ⊘ | ⊘ | - | ● | ⊘ | - | ○ |
| 29 | T | ⊘ | ○ | ○ | ⊘ | ⊘ | ○ | ● | - | ⊘ | ⊘ |
|    | P | ⊘ | ○ | ○ | ⊘ | ⊘ | ○ | ● | - | ⊘ | ⊘ |
| 32 | T | ⊘ | ● | - | ● | ● | ⊘ | ● | ● | ⊘ | ○ |
|    | P | ⊘ | ● | - | - | ○ | ⊘ | ○ | - | ⊘ | ○ |
| 33 | T | ⊘ | ● | - | ○ | ⊘ | ○ | ○ | ○ | ● | ● |
|    | P | ⊘ | ● | - | ○ | ⊘ | ○ | ○ | - | ● | - |
| 34 | T | ⊘ | ● | ○ | ● | ⊘ | ⊘ | ● | ⊘ | ○ | ● |
|    | P | ⊘ | ● | ○ | ● | ⊘ | ⊘ | ○ | ⊘ | ○ | ○ |
| 35 | T | ⊘ | ○ | ⊘ | ○ | ○ | ○ | ○ | ○ | ● | ○ |
|    | P | ⊘ | ○ | ⊘ | - | ○ | ○ | ○ | ○ | ● | ○ |
| 36 | T | ○ | ○ | ● | ⊘ | ○ | ⊘ | ○ | ⊘ | ⊘ | ○ |
|    | P | ○ | ○ | ● | ⊘ | ○ | ⊘ | ○ | ⊘ | ⊘ | ○ |
| 37 | T | - | ⊘ | ● | - | ○ | ⊘ | ○ | ● | - | ⊘ |
|    | P | - | ⊘ | ● | ○ | ● | ⊘ | - | ● | - | ⊘ |
| 39 | T | ○ | ● | ● | - | ○ | ● | ⊘ | ○ | - | - |
|    | P | ○ | ● | ● | ○ | ○ | - | ⊘ | - | - | - |
| 40 | T | ● | ⊘ | ○ | ○ | ⊘ | ○ | ○ | - | ○ | ● |
|    | P | ● | ⊘ | ○ | ○ | ⊘ | ○ | ○ | - | ○ | ● |

LOH status of tumor (T) and plasma (P) DNA are indicated by the following:
● =LOH    ⊘ =Homozygous    ○ =Retention    - : undetermined;

Forty patients matched tumor and plasma were assessed. Only those patients with at least one LOH defined at microsatellite locus in plasma are shown.

FIG. 2

DETECTION OF LOSS OF HETEROZYGOSITY IN TUMOR AND SERUM OF MELANOMA PATIENTS

1. FIELD OF THE INVENTION

The present invention is related to the fields of molecular biology and oncology and provides methods for diagnosis, staging and monitoring of melanoma patients.

2. DESCRIPTION OF RELATED ART

Cancer cells almost invariably undergo a loss of genetic material (DNA) when compared to normal cells. This deletion of genetic material which almost all, if not all, varieties of cancer undergo is referred to as "loss of heterozygosity" (LOH). The loss of genetic material from cancer cells can result in the selective loss of one of two or more alleles of a gene vital for cell viability or cell growth at a particular locus on the chromosome. All genes, except those of the two sex chromosomes, exist in duplicate in human cells, with one copy of each gene (allele) found at the same place (locus) on each of the paired chromosomes. Each chromosome pair thus contains two alleles for any gene, one from each parent. This redundancy of allelic gene pairs on duplicate chromosomes provides a safety system; if a single allele of any pair is defective or absent, the surviving allele will continue to produce the coded protein.

Due to the genetic heterogeneity or DNA polymorphism, many of the paired alleles of genes differ from one another. When the two alleles are identical, the individual is said to be homozygous for that pair of alleles at that particular locus. Alternatively, when the two alleles are different, the individual is heterozygous at that locus. Typically both alleles are transcribed and ultimately translated into either identical proteins in the homozygous case or different proteins in the heterozygous case. If one of a pair of heterozygous alleles is lost due to a deletion of DNA from one of the paired chromosomes, only the remaining allele will be expressed and the affected cells will be functionally homozygous. This situation is termed a "loss of heterozygosity" (LOH) or reduction to homozygosity. Following this loss of an allele from a heterozygous cell, the protein or gene product thereafter expressed will be homogeneous because all of the protein will be encoded by the single remaining allele. The cell becomes effectively homozygous at the gene locus where the deletion occurred. Almost all, if not all, cancer cells undergo LOH at some chromosomal regions.

Through the use of DNA probes, DNA from an individual's normal cells can be compared with DNA extracted from the same individual's tumor cells and LOH can be identified using experimental techniques well known in the art. Alternatively, LOH can be assayed by demonstrating two polymorphic forms of a protein in normal heterozygous cells, and only one form in cancer cells where the deletion of an allele has occurred. See for example Lasko, 1991.

Recent advances in molecular biology have revealed that genesis and progression of tumors follow an accumulation of multiple genetic alterations, including inactivation of tumor suppresser genes and/or activation of proto-oncogenes. There are over 40 known proto-oncogenes and suppresser genes to date, which fall into various categories depending on their functional characteristics. These include, growth factors and growth factor receptors, messengers of intracellular signal transduction pathways, for example, between the cytoplasm and the nucleus, and regulatory proteins influencing gene expression and DNA replication.

Frequent loss of heterozygosity (LOH) on specific chromosomal regions has been reported in many kinds of malignancies, which indicates the existence of putative tumor suppresser genes or tumor-related genes on or near these loci. LOH analysis is a powerful tool to search for a tumor suppresser gene by narrowing and identifying the region where a putative gene exists. By now, numerous LOH analyses, combined with genetic linkage analysis on pedigrees of familial cancer (Vogelstein, 1988; Fearon, 1990; Friend, 1986) or homozygous deletion analyses (Call, 1990; Kinzler, 1991; Baker, 1989) have identified many kinds of candidate tumor suppresser or tumor-related genes. Also, because allelic losses on specific chromosomal regions are the most common genetic alterations observed in a variety of malignancies, microsatellite analysis has been applied to detect DNA of cancer cells in specimens from body fluids, such as sputum for lung cancer and urine for bladder cancer. (Rouleau, 1993; Latif, 1993) Moreover, it has been established that markedly increased concentrations of soluble DNA are present in plasma of individuals with cancer and some other diseases, indicating that cell free serum or plasma can be used for detecting cancer DNA with microsatellite abnormalities. (Kamp, 1994; Steck, 1997) Two groups have reported microsatellite alterations in plasma or serum of a limited number of patients with small cell lung cancer or head and neck cancer. (Hahn, 1996; Miozzo, 1996)

Recent developments in cancer therapeutics have demonstrated the need for more sensitive staging and monitoring procedures to ensure initiation of appropriate treatment, to define the end points of therapy and to develop and evaluate novel treatment modalities and strategies. In the management of melanoma patients, the choice of appropriate initial treatment depends on accurate assessment of the stage of the disease. Patients with limited or regional disease generally have a better prognosis and are treated differently than patients who have distant metastases (Minna, 1989). However, conventional techniques to detect these metastases are not very sensitive, and these patients are often not cured by primary tumor resection because they have metastases that are not identified by standard methods during preoperative staging. Thus, more sensitive methods to detect metastases in other types of carcinomas would identify patients who will not be cured by local therapeutic measures, for whom effective systemic therapies would be more appropriate.

The strategy of the present invention is to utilize genetic differences between normal and cancer cells for diagnosis and monitoring of melanoma patients. Many genes coding for proteins or other factors vital to cell survival and growth that are lost, can be identified through LOH analysis of microsatellite loci in cancer cells and mapped to specific chromosomal regions. In melanoma, mutations of several already-known tumor suppresser genes such as p53 gene, neurofibromatosis 1 (NF1) gene, and NF2 gene have been reported at a low frequency and deletions and/or mutations of the cyclin dependent kinase 4 (CDK4) inhibitor gene, which is a responsible tumor suppresser gene for a familial melanoma, have been thought to be important genetic changes in tumor development. (Miozzo, 1996) In addition to the locus of CDK4 inhibitor gene (9p21), frequent chromosomal deletions have been reported on 1p36, 3p25, 6q22-q26, 10q24-q26, and 11q23. (Mao, 1996; Stroun, 1987; Chen 1996; Nawroz, 1996)

Thus, an efficient method of testing DNA microsatellite loci for LOH allows early diagnosis of melanoma patients and monitoring of the progression of the disease as well as effectiveness of the therapeutic regimen.

3. SUMMARY

It is an object of the invention to provide methods for identifying and assessing the extent of genetic change in neoplastic tissue. More specifically, the present invention provides methods for early diagnosis, staging and monitoring tumor progression and tumor genetic instability of melanoma patients by detecting the loss of a specified set of polymorphic alleles (LOH), alone or in combinations, in DNA from plasma and serum. In a preferred embodiment, this method comprises the steps of (a) in a sample of biological fluid, amplifying nucleic acid from an LOH marker, if present, (b) detecting the presence or absence of the LOH marker, and (c) correlating the findings with the occurrence and/or progression of melanoma. In a preferred embodiment of the present invention, the set of alleles which are tested for LOH are selected from the group consisting of D1S214, D1S228, D3S1293, D6S264, D9S157, D9S161, S10S212, D10S216, D11S925. In addition, combinations of the alleles, including D9S157 combined with D3S1293, D9S157 combined with D1S228, D1S925 combined with D3S1293, and all alleles are tested.

It is another object of the invention to provide a kit for diagnosing, staging and monitoring melanoma patients. In a preferred embodiment of the invention, a kit is provided comprising a set of nucleic acid probes for specified alleles for which the patient is homozygous or heterozygous to detect LOH in these specified alleles. This will provide a measure of the extent of genetic change in the neoplastic tissue which can be correlated with a prognosis. In one specific embodiment, the presence or absence of a specific allele or combination of alleles is tested by amplification of regions of the DNA using pairs of primers which bracket specific regions of DNA on specific chromosome arms containing repeat sequences with polymorphism. Preferably the assay uses fluorescent labeling of DNA with multiple types of chromophores. However, radioactive and other labeling techniques known in the art also may be used.

This invention provides a logistically practical assay to monitor the genetic changes during melanoma progression. The events of tumor progression are dynamic and the genetic changes that concurrently occur also are very dynamic and complex. The most significant advantage of this approach compared to other approaches in the ability to monitor disease progression and genetic changes without assessing the tumor. This is particularly important during early phases of distant disease spread, in which subclinical disease is undetectable by conventional imaging techniques. In addition, in advance stage diseases or inoperable sites in which tumor tissue is very difficult or impossible to obtain for genetic analysis, the present invention provides an alternative for assessing LOH.

4. BRIEF DESCRIPTION OF FIGURES

FIG. 1. Different allelic pattern shown in a matched patient tumor biopsy and plasma. Analysis of individual patients' DNA: N, lymphocytes; P, plasma; and T, microdissected primary melanoma lesion.

FIG. 2. Representative frequency of LOH in plasma and tumor of advanced melanoma patients at 10 individual microsatellite loci. Markers examined are indicated at the top of the figure.

Figure 3:
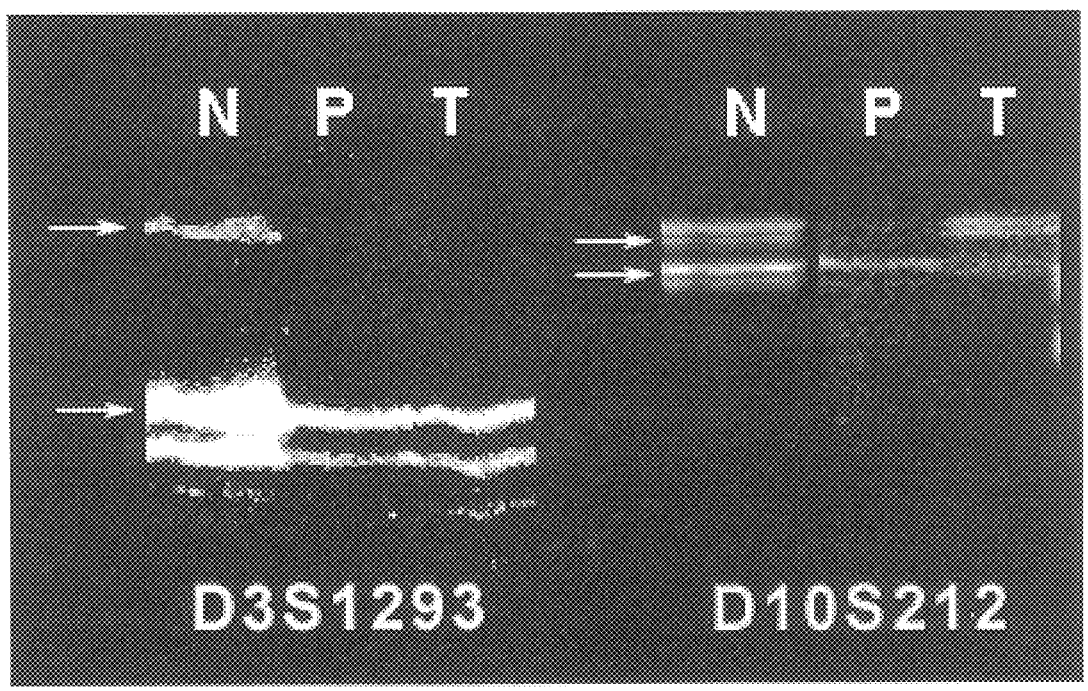

FIG. 3. Allelic losses in tumor and plasma at individual microsatellite loci; analysis for individual patients' paired specimens: N, lymphocytes; T, melanoma tumor; and P, plasma. Arrows indicate the position of the deleted alleles. Markers are indicated below.

5. DETAILED DESCRIPTION OF THE PREFERRED EMBODIMENTS

Definitions

The expression "amplification of polynucleotides" includes methods such as polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis (1990) for PCR, and Wu (1989) for LCR. Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf (1986).

The term "complementary" means that one nucleic acid is identical to, or hybridizes selectively to, another nucleic acid. A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. See, for example, Sambrook et al., Molecular Cloning: A Laboratory Manual (2nd ed.), Vols. 1–3, Cold Spring Harbor Laboratory, (1989) or Current Protocols in Molecular Biology, F. Ausubel et al., ed. Greene Publishing and Wiley-Interscience, New York (1987), both of which are incorporated herein by reference. Typically, selective hybridization will occur when there is at least about 55% identity over a stretch of at least 14–25 nucleotides, preferably at least about 65%, more preferably at least about 75%, and most preferably at least about 90%. See also, Kanehisa (1984).

The term "denaturing" refers to the process by which strands of oligonucleotide duplexes are no longer base-paired by hydrogen bonding and are separated into single-stranded molecules. Methods of denaturation are well known to those skilled in the art and include thermal denaturation and alkaline denaturation.

The term "hybridization" refers to two nucleic acid strands associated with each other which may or may not be fully base-paired. Various degrees of stringency of hybridization may be employed. The more severe the conditions, the greater the complementarity that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 800° C., usually 30° C. to 75° C. (see, for example, Current Protocols in Molecular Biology, Ausubel, ed., Wiley & Sons, 1989).

The terms "isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. Current Protocols in Molecular Biology, Greene Publishing and Wiley-Interscience, New York (1987), incorporated herein by reference.

The term "nucleic acid probes" may be DNA fragments prepared, for example, by PCR, or synthesized by either the phosphoramidite method described by Beaucage and Carruthers (1981), or by the triester method according to Matteucci (1981), both incorporated herein by reference. A double-stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included.

An "LOH marker" is DNA from a microsatellite locus, a deletion, alteration, or amplification in which, when compared to normal cells, is associated with cancer or other diseases. An LOH marker often is associated with loss of a tumor suppressor gene or another, usually tumor related, gene.

The term "microsatellites" refers to short repetitive sequences of DNA that are widely distributed in the human genome. Somatic alterations in the repeat length of such microsatellites have been shown to represent a characteristic feature of tumors.

The present invention relates to a method of detecting LOH in biological fluids, wherein the presence of LOH is associated with the occurrence of melanoma. This method represents a significant advance over such techniques as tissue biopsy by providing a non-invasive, rapid, and accurate method for detecting LOH of specific alleles associated with melanoma. Thus, the present invention provides a method which can be used to screen high-risk populations and to monitor high risk patients undergoing chemoprevention, chemotherapy, immunotherapy or other treatments.

A preferred method of the invention involves the initial steps of obtaining a sample of biological fluid (e.g., urine, blood plasma or serum, sputum, cerebral spinal fluid), then deproteinizing and extracting the DNA. The mutant nucleotide sequence to be amplified, may be a fraction of a larger molecule or can be present initially as a discrete molecule. Where the target mutant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means. If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands.

According to the method of the present invention, DNA is isolated from plasma/serum of a melanoma patient. For comparison, DNA samples isolated from neoplastic tissue and a second sample is isolated from non-neoplastic tissue from the same patient (control), for example, lymphocytes. The non-neoplastic tissue can be of the same type as the neoplastic tissue or from a different organ source. It is desirable that the neoplastic tissue contains primarily neoplastic cells and that normal cells be separated from the neoplastic tissue. Ways for separating cancerous from non-cancerous cells are known in the art and include, for example, microdissection of tumor cells from normal cells of tissues, DNA isolation from paraffin sections and cryostat sections, as well as flow cytometry to separate aneuploid cells from diploid cells. DNA can also be isolated from tissues preserved in parafin. Separations based on cell size or density may also be used. Once the tissues have been microdissected, DNA can be isolated from the tissue using any means known in the art. The tissue can be minced or homogenized and then the resulting cells can be lysed using a mixture of enzyme and detergent, see for example Maniatis, Molecular Cloning, a Laboratory Manual, Cold Spring Harbor Laboratory, 1982. The nucleic acids can be extracted using standard techniques such as phenol and chloroform extraction, and ethanol precipitation.

Testing for the loss of a particular allele can be accomplished by a number of means. It is desirable that the alleles used in the allelotype loss analysis be those for which the patient is heterozygous. Determination of heterozygosity is well within the skill of the art and includes examining the second sample of DNA which is isolated from non-neoplastic tissue of the patient and noting the size, number of bands (1 or 2), or level of amplification of signal (decrease) of individual bands.

One means of testing for loss of an allele is by digesting the DNA sample and a known heterozygous DNA sample with a restriction endonuclease. Restriction endonucleases are well known in the art for their ability to cleave DNA at specific sequences, and thus generate a discrete set of DNA fragments from each DNA sample. The restriction fragments of each DNA sample can be separated by any means known in the art. For example, agarose or polyacrylamide gel electrophoresis can be used to electrophoretically separate fragments according to physical properties such as size. The restriction fragments can be hybridized to nucleic acid probes which detect restriction fragment length polymorphisms (RFLP), as described above. There are various hybridization techniques known in the art, including both liquid and solid phase techniques. One particularly useful method employs transferring the separated fragments from an electrophoretic gel matrix to a solid support such as nylon or filter paper so that the fragments retain the relative orientation which they had on the electrophoretic gel matrix. The hybrid duplexes can be detected by any means known in the art, for example, by autoradiography if the nucleic acid probes have been radioactively labeled. Other labeling and detection means are well known in the art and may be used accordingly.

An alternative means for testing for the presence of allelic deletions is by using PCR (polymerase chain reaction, see also, U.S. Pat. Nos. 4,683,195; 4,683,202; and 4,683,194, which are incorporated by reference herein). This method allows amplification of discrete regions of DNA containing microsatellite sequences. Amplification is accomplished by annealing, i.e., hybridizing a pair of single stranded primers, usually comprising DNA, to the DNA of said first and second samples from a patient. The primers embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. More specifically, the primers are designed to be "substantially" complementary to each strand of target nucleotide sequence to be amplified. Substantially complementary means that the primers must be sufficiently complementary to hybridize with their respective strands (i.e. with the flanking sequences) under conditions which allow amplification of the nucleotide sequence to occur. The primer is preferably single stranded for maximum efficiency in amplification but may be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primers for use in the present invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22: 1859–1862, 1981). One method for synthesizing oligonucleotides on a modified solid support is described in U.S. Pat. No. 4,458,066. The primers are annealed to opposite strands of the DNA sequence containing an LOH marker, such that they prime DNA synthesis in opposite but convergent directions on a chromosome. Amplification of the region containing the LOH marker is accomplished by repeated cycles of DNA synthesis. Experimental conditions conducive to synthesis include the presence of nucleoside triphosphates and an agent for polymerization, such as DNA polymerase, and a suitable temperature and pH. Preferably the DNA polymerase is Taq polymerase which is relatively heat insensitive. The amplification procedure includes a specified number of cycles of amplification in a DNA thermal cycler. After an initial denaturation period of 5 minutes, each amplification cycle preferably includes a denaturation period of about 1 minute at 95° C., primer annealing for about 2 minutes at 58° C. and an extension at 72° C. for approximately 1 minute. Following the amplification, aliquots of amplified DNA from the PCR can be analyzed by techniques such as electrophoresis through agarose gel using ethidium bromide staining. Improved sensitivity may be attained by using labeled primers and subsequently identifying the amplified product by detecting radioactivity or chemiluminescense on film.

In a preferred embodiment, the assay involves labeling of the PCR primers with multiple types of chromophore dyes. In another embodiment, the PCR primers are labeled with an atom or inorganic radical, most commonly using radionuclides, but also perhaps heavy metals. Radioactive labels include $^{32}P$, $^{125}I$, $^{3}H$, $^{14}C$, or any radioactive label which provides for an adequate signal and has sufficient half-life. Other labels include ligands, which can serve as a specific binding pair member for a labeled ligand, and the like.

As used herein, allele-specific amplification describes a feature of the method of the invention where primers are used which are specific to an LOH marker, thus enabling amplification of the sequence to occur where there is 100% complementarity between the 3' end of the primer and the target gene sequence.

Loss of an allele is ultimately determined by comparing the pattern of bands corresponding to the allele in the normal tissue to the neoplastic tissue or biological fluid (ie. plasma/serum) and quantitation provides a predictive measure of metastasis, tumor recurrence, and resulting death.

Any LOH marker may be used in the method and kit of the present invention. In a preferred embodiment of the present invention, the set of alleles which are tested for LOH are selected from the group consisting of D1S214, D1S228, D3S1293, D6S264, D9S157, D9S161, S10S212, D10S216, D11S925. In a further preferred embodiment of the present invention, combinations of the alleles, including D9S157 combined with D3S1293, D9S157 combined with D1S228, D11S925 combined with D3S1293; and a combination of all listed alleles are tested. In a further embodiment of the present invention, other alleles, and combinations of alleles, now known in the art or identified in the future are tested for LOH.

Because the method of the present invention requires only DNA extraction from bodily fluid such as blood, it can be performed at any time and repeatedly on a single patient. Blood can be taken and monitored for LOH before or after surgery; before, during, and after treatment, such as chemotherapy, radiation therapy, gene therapy or immunotherapy; or during follow-up examination after treatment for disease progression, stability, or recurrence. The method of the present invention also may be used to detect subclinical disease presence or recurrence with an LOH marker specific for that patient since LOH markers are specific to an individual patient's tumor. The method also can detect if multiple metastases may be present using tumor specific LOH markers.

In another aspect, the present invention can be provided in a kit format for detecting metastatic melanomas and carcinomas in selected body tissues and fluids. Such a kit may comprise a carrier means being compartmentalized to receive in close confinement one or more container means such as vials, tubes, and the like, each of the container means comprising one of the separate elements to be used in the method. Such elements include a labeled primer pair for amplifying an LOH marker. The kit also may include an enzyme for reverse transcribing RNA to provide cDNA, a DNA polymerase for amplifying the target DNA, appropriate amplification buffers and deoxyribonucleoside triphosphates. The nucleic acids in said kits may be provided in solution or lyophilized form. Preferably, the nucleic acids will be sterile and devoid of nucleases to maximize shelf-life.

The publications and other reference materials referred to herein describe the background of the invention and provide additional detail regarding its practice and are hereby incorporated by reference. For convenience, the reference materials are referenced and grouped in the appended bibliography. The present invention is further described in the following example. The example is for illustrative purposes only, and is not to be construed as limiting the scope of the invention as set forth in the appended claims. It is provided merely to teach concrete and practical means for carrying out the invention.

EXAMPLE I

Sample Collection

Five-milliliter (ml) blood samples were collected in 0.129 M sodium citrate from a total of 76 patients, who have been followed up with a diagnosis of advance stage melanoma and 20 healthy subjects. The plasma was immediately separated from the blood cells by centrifugation at 1000×g, for 5 minutes, filtered through a 13 mm serum filter, and kept at −30° C. until DNA extraction. White blood cells from individual patients were used as a normal DNA control. Lymphocytes were separated from red blood cells with Puregene RBC Lysis Solution (Gentra Systems, MN). Blood also was spotted onto FTA blood stain cards for normal genomic DNA extraction as well as long term storage. The cell pellet was washed with physiological phosphate buffered saline. Corresponding tumor tissues were microdissected from 10 mm serial sections of formalin fixed paraffin embedded blocks. All tissue sections were diagnosed to include malignant melanoma cells by histopathology (Kuroki, 1995).

DNA Isolation

Control lymphocytes DNA was isolated by using DNAzol™ (Molecular Research Center Inc., Ohio). In brief, cell pellets were homogenized with 1 ml DNAzol™ and precipitated by the addition of 0.5 ml of 100% ethanol. After centrifugation, precipitated DNA was washed twice with 95% ethanol and suspended in TE buffer. One ml plasma was diluted at 60% with a solution of 0.9M NaCl, 1% SDS and proteinase K, and was shaken at 37° C. overnight in the presence of an equal volume of phenol-chloroform-isoamylalcohol (25:24:1). After centrifugation for 15 min. at 1000×g, the aqueous phase was collected, extracted with an equal volume of phenol-chloroform-isoamylalchol again, and followed by isopropanol-precipitation. Tumor tissues which had been micro-dissected from 40 paraffin blocks, were incubated with xylenes at 37° C. overnight. The pellet was recovered after centrifugation, and washed twice with 1 ml 100% ethanol. The remaining material was dried by vacuum centrifugation, incubated with proteinase K in lysis buffer (50 mm Tris HCl, 1 mm EDTA, and 0.5% Tween 20) at 37° C. overnight, and then boiled at 95° C. for 10 minutes in a heat block. After phenol-chloroform-isoamyl extraction, DNA was recovered by ethanol precipitation.

Microsatellite Markers and PCR

Primer sets for PCR amplification of microsatellite markers were chosen on six chromosome arms. (Gyapay, 1994; Hol, 1992). The following $CA_n$-repeat microsatellite markers were used: D1S214 and D1S288 on 1p36, D3S1293 on 3p25, D6S264 at 6q2-q27; D9S157 and D9S161 on 9p21; D10S212 and D10S216, on 10q24-q26, and D11S925 on 11q23. Primer sets for PCR were obtained from Research Genetics, Inc. (Human Huntsville, Ala.) in which the sense primer had been labeled with fluorescent dye: FAM or Cy5. Genomic DNA (50 ng) was amplified by the polymerase chain reaction (PCR) in 25 µl-reaction containing 1×PCR buffer (6.7 mM Tris, 16.6 mM ammonium sulphate, 6.7 mM EDTA, 10 mM β-mercaptoethanol), 6 pmol each of primers, 0.1 U Taq DNA polymerase, 0.8 mM each dNTP, and 1.5 mM $MgCl_2$. Forty rounds of PCR cycling were performed with each cycle consisting of 30 seconds at 94° C., 30 seconds at 50–55° C., and 30 seconds at 72° C. and followed by a final extension step of 72° C. for 5 minutes. The PCR products at each locus are described in Table 1.

TABLE 1

Microsatellite [(ca) repeat] Markers used for LOH Analysis

| Locus | Chromosome Location | PCR Product Size Range (base pairs) | Repeat # of (CA) motif |
|---|---|---|---|
| D1S214 | 1p36 | 120–142 | 14–25 |
| D1S228 | 1p36 | 117–129 | 14–20 |
| D3S1293 | 3p25 | 116–144 | 10–24 |
| D6S264 | 6q22-q26 | 108–122 | 14–21 |
| IQFIIR | 6q25-q27 | 158–168 | 13–18 |
| D9S157 | 9p21 | 133–149 | 14–22 |
| D9S161 | 9p21 | 119–135 | 18–25 |

TABLE 1-continued

Microsatellite [(ca) repeat] Markers used for LOH Analysis

| Locus | Chromosome Location | PCR Product Size Range (base pairs) | Repeat # of (CA) motif |
|---|---|---|---|
| D10S212 | 10q26 | 189–201 | 12–18 |
| D10S216 | 10q24 | 202–225 | 11–22 |
| D11S925 | 11q23 | 173–199 | 15–28 |

LOH Analysis.

Five µl of each PCR product, mixed with 2 µl of loading dye (100% formamide, 2 mM EDTA, 2% dextrane blue), was incubated at 95° C. for 15 minutes. The concentrated samples were electrophoresed in 6% denaturing PAGE, containing 7.7M urea at 1600V for 2 hours. The image of fluorescent-labeled PCR products was scanned and acquired by a fluorescent/optical scanner, GenomyxSC (Genomyx Corp, Foster City, Calif.). After the image acquisition was completed, we analyzed the image files using Adobe Photoshop™ software (Microsoft, San Jose, Calif.). Densitometric analysis was performed with imaging software ClaritySC (Media Cybernetics, Maryland). Calculation and comparing intensity of the specific alleles in lymphocytes, plasma, and tumor DNA were performed to evaluate for LOH. Tumor and plasma were scored as exhibiting LOH, if there was an absence or a more than 50% reduction in intensity of one allele in these specimens compared to the respective allele in normal matched lymphocytes. (Fujiwara, 1993)

Statistics.

Correlations between patients' matched tumor and plasma analysis for individual microsatellite markers were assessed using Kappa agreement test. Logistic regression was used to test the association between number of positive markers and AJCC Stage. Spearman correlation was estimated to evaluate the association between number of positive markers, Breslow thickness and Clark Level. Chi-square test was also used when data was cross-classified into a contingency table.

LOH Analysis in Plasma and Melanoma Tumor Biopsies.

LOH was initially assessed at 10 different loci on six different chromosomes in paired tumor biopsies and plasma from 40 melanoma patients. DNA was extracted and detected from all patients' plasma, tumor biopsies and lymphocytes. Frequency of LOH varied 23–53% in tumor biopsies and 4–33% in plasma for individual microsatellite markers from informative cases. The most frequent microsatellite markers with LOH were detected at loci D6S264, D9S161, D10S216, and D11S925, respectively, in informative melanoma tumors (Table 2). The most frequent microsatellite markers with LOH were detected at loci D10S216, D3S1293, D6S264 and D1S214, respectively, in informative plasmas from melanoma patients (Table 2). Microsatellite markers D6S264 and D10S216 were in the top four frequent loci with LOH for both plasma and tumor. Representative LOH in tumor and plasma as compared with lymphocytes DNA is shown in FIGS. 1 and 3. Twenty healthy donors lymphocyte and plasma DNA was assessed for microsatellite markers and no LOH was observed in either type of sample.

TABLE 2

Microsatellite Analysis of Paired Tumor and Plasma DNA In Melanoma Patients

| Locus | Chromosome Location | LOH in tumor/informative cases (%) | LOH in plasma/informative cases (%) |
| --- | --- | --- | --- |
| D1S214 | 1p36 | 9/24 (38%) | 5/25 (20%) |
| D1S228 | 1p36 | 8/24 (33%) | 5/26 (19%) |
| D3S1293 | 3p25 | 6/17 (35%) | 6/21 (29%) |
| D6S264 | 6q22-q26 | 8/15 (53%) | 4/15 (27%) |
| IGFIIR | 6q25-q27 | 5/22 (23%) | 1/25 (4%) |
| D9S157 | 9p21 | 11/28 (39%) | 3/30 (10%) |
| D9S161 | 9p21 | 11/25 (44%) | 5/26 (19%) |
| D10S212 | 10q26 | 6/15 (40%) | 1/11 (9%) |
| D10S216 | 10q24 | 5/12 (42%) | 4/12 (33%) |
| D11S925 | 11q23 | 9/22 (41%) | 2/24 (8%) |

The summary of LOH in tumor and plasma from 40 melanoma patients using the panel of 10 microsatellite markers is shown in Table 3. In 36/40 (90%) 40 tumors and in respective 23/40 (58%) plasmas of informative cases showed LOH for at least one microsatellite marker. Overall, comparison of LOH in matched paired plasma and tumor specimens of each individual microsatellite marker showed a significant correlation (p<0.0001). This indicates plasma analysis for LOH can be used in place of tumor tissue and the results are valid.

TABLE 3

Microsatellite Analysis and Clinical Status of Melanoma Patients

| Patient # | Tumor LOH | Plasma LOH | AJCC Stage at blood draw | Clinical Status at blood draw | AJCC Stage at Follow-up | Clinical Status at follow-up |
| --- | --- | --- | --- | --- | --- | --- |
| 1 | + | − | 4 | AWD | 4 | Deceased |
| 2 | + | + | 4 | NED | 4 | NED |
| 3 | + | − | 4 | AWD | 4 | Deceased |
| 4 | + | + | 4 | NED | 4 | NED |
| 5 | + | + | 4 | NED | 4 | NED |
| 6 | + | − | 4 | AWD | 4 | AWD |
| 7 | + | + | 4 | NED | 4 | NED |
| 8 | + | − | 4 | NED | 4 | NED |
| 9 | + | − | 3 | NED | 3 | AWD |
| 10 | − | + | 3 | NED | 3 | NED |
| 11 | + | + | 3 | NED | 3 | NED |
| 12 | + | + | 3 | NED | 3 | NED |
| 13 | + | + | 4 | NED | 4 | NED |
| 14 | − | + | 3 | NED | 3 | NED |
| 15 | + | − | 3 | AWD | 3 | AWD |
| 16 | + | − | 3 | NED | 4 | AWD |
| 17 | + | − | 3 | NED | 4 | AWD |
| 18 | + | + | 3 | NED | 4 | NED |
| 19 | + | − | 3 | NED | 4 | AWD |
| 20 | + | − | 4 | NED | 4 | AWD |
| 21 | + | + | 4 | AWD | 4 | AWD |
| 22 | − | − | 4 | AWD | 4 | AWD |
| 23 | + | − | 4 | AWD | 4 | NED |
| 24 | − | − | 4 | AWD | 4 | AWD |
| 25 | − | − | 4 | NED | 4 | NED |
| 26 | + | + | 3 | NED | 4 | AWD |
| 27 | + | + | 3 | NED | 3 | NED |
| 28 | + | + | 3 | NED | 3 | NED |
| 29 | + | + | 4 | AWD | 4 | AWD |
| 30 | + | − | 3 | NED | 3 | NED |
| 31 | + | − | 4 | NED | 4 | NED |
| 32 | + | + | 4 | AWD | 4 | NED |
| 33 | + | + | 2 | NED | 4 | AWD |
| 34 | + | + | 4 | NED | 4 | NED |
| 35 | + | + | 4 | AWD | 4 | NED |
| 36 | + | + | 4 | AWD | 4 | AWD |
| 37 | + | + | 4 | AWD | 4 | Deceased |
| 38 | − | − | 3 | NED | 3 | NED |
| 39 | + | + | 4 | NED | 4 | AWD |
| 40 | + | + | 4 | AWD | 4 | AWD |

LOH +: LOH was detected at least at one locus.
LOH −: LOH was not detected at any loci.

A summary of all patients in which LOH occurred in a minimum of one loci in plasma is shown in FIG. 2. Seventeen of 23 patients showed LOH common in both tumor and plasma at all loci. The remaining 6 patients showed some discrepancy of LOH pattern between tumor and plasma. There were differences in some patients in comparison of LOH in tumor and plasma in which LOH was observed in tumor and not plasma, and vice versa. In one interesting case, the plasma DNA showed LOH at D3S1293 but no LOH at D9S157, whereas tumor of this patient showed LOH at both loci. These differences may be due to different metastases at various sites or clonal heterogeneity within the tumor.

Plasma LOH Correlation with Different Clinical Stages of Melanoma

Plasma was assessed from 76 melanoma patients with different clinical stages (AJCC) of disease: 7 Stage I; 13 Stage II; 29 Stage III; and 27 Stage IV. The mean age of the patients was 51.6±17.0 SD consisting of 25 females and 48 males. Breslow thickness distribution was broken down as follows: <=0.75 (n=8); 0.76–1.5 (n=26); 1.5–4 (n=21); >4 (n=6); missing (n=15). The Clark level of distribution was: level II (n=10); level III (n=18); level IV (n=29); level V (n=8); missing (n=11). The correlation between frequency of plasma LOH in informative patient cases and AJCC stage was performed (Table 4). The frequency of LOH was higher in more advanced stages of disease: 5/19 (26%) patients with stage I and II had LOH whereas, 33/57 (58%) patients in stage III/IV had LOH at least in one locus. One interesting finding observed in a Stage I patient plasma and primary tumor where LOH was detected at loci D3S1293 and D10S212 was the different pattern of allele in the tumor and plasma (FIG. 3). The longer allele was deleted in both plasma and tumor for D3S1293 whereas, the deleted allele was different in the plasma and tumor (longer allele in plasma and shorter allele in tumor) for D10S212.

TABLE 4

Correlation between LOH in Plasma and AJCC Stage

| AJCC Stage | LOH+ % | LOH− % | Total |
| --- | --- | --- | --- |
| I | 2 (29%) | 5 (71%) | 7 |
| II | 3 (25%) | 9 (75%) | 12 |
| III | 16 (53%) | 14 (47%) | 30 |
| IV | 17 (63%) | 10 (37%) | 27 |

LOH (+): At least one locus was detected as LOH.

Various analyses were performed to determine if the frequency of LOH in plasma correlated to clinical stage and known prognostic factors of melanoma. Assessment of clinical stage to individual microsatellite markets showing LOH in patients plasma was performed. Overall, there was a significant correlation of number of LOH (positive) markers with AJCC Stage in the 76 plasma samples (p=0.02).

Only at the single loci D3S1293 there was a significant correlation (p=0.02) with advancement of clinical stage of disease. The next closest correlation was of LOH at D1S228 (p=0.065). In the assessment of different clinical stages of disease to microsatellite marker combinations showing LOH, the combination of D9S157 and D3S1293 (p=0.01), D9S157 and D1S228 (p=0.05), D11S925 and D3S1293 (p=0.01) had significant correlations. The LOH combination of D1S228 and D3S1293 approached significance (p=0.07).

REFERENCES

Baker, S J., Fearon, E R., Nigro, J M., Hamilton, S R., Preisinger, A C., Jessup, J M., van Tuinen, P., Ledbetter, D H., Baker, D F., Nakamura, Y., White, R., and Vogelstein, B. Chromosome 17 deletions and p53 gene mutations in colorectal carcinomas. Science (Washington DC), 244, 217–221 (1989).

Beaucage and Carruthers, Tetrahedron Lett. 22:1859–1862 (1981)

Call K M, Glaser T, Ito C Y, Buckler A J, Pelletier J, Haber D A, Rose E A, Kral A, Yeger H, Lewis W H, et al. Isolation and characterization of a zinc finger polypeptide gene at the human chromosome 11 Wilms' tumor locus. Cell 60, 509–520 (1990).

Chen, X Q., Stroun, M., Magnenat, J L., Nicod, L P., Kurt, A M., Lyautey, J., Lederrey, C., and Anker, P. Microsatellite alterations in plasma DNA of small cell lung cancer patients. Nature Med. 2, 1033–1035 (1996).

Fearon, E R., and Vogelstein, B. A genetic model for colorectal tumorigenesis. Cell 61, 759–767 (1990).

Friend S H, Bernards R, Rogelj S, Weinberg R A, Rapaport J M, Albert D M, Dryja T P., A human DNA segment with properties of the gene that predisposes to retinoblastoma and osteosarcoma. Nature 323 (6089), 643–646 (1986).

Gyapay, G., Morissette, J., Vignal, A., Dib, C., Fizames, C., Millasseau, P., Marc, S., Bernardi, G., Lathrop, M., Wissenbach, J. The 1993–94 Genethon human genetic linkage map. Nature Genet. 70, 246–339 (1994).

Hahn, S A., Schutte, M., Hoque, A T M S., Moskaluk, C A., da Costa, L T., Rozenblum, E., Weinstein, C L., Fischer, A., Yeo, C J., Hruban, R H., Kern, S E. DPC4, a candidate tumor suppressor gene at human chromosome 18q21.1. Science (Washington D.C.) 271, 350–353 (1996).

Hol, F A., Geurds, M P A., Hamel, B C J., and Mariman, E C M. Improving the polymorphism content of the 3' UTR of the human IGFIIR gene. Human Mol. Gnet. 1, 347 (1992).

Innis et al. (1990) PCR Protocols: A Guide to Methods and Applications, Academic Press, San Diego.

Kamp, A., Gruis, N A., Weaver-Feldhaus, J., Liu, Q., Harshman, K., Tavtigian S V., Stocker, E., Day, R S., 3rd, Johnson, B E., and Skolnick, M H. A cell cycle regulator potentially involved in genesis of many tumor types. Science (Washington D.C.) 264, 436–440 (1994).

Kanehisa M., Nucleic Acids Res. 12:203 (1984)

Kinzler, K., Nilbert, M C., Su, L., Vogelstein, B., Bryan T M. Levy, D B., Smith, K J., Preisinger, A C., Hedge, P., McKechnie, D., Finniear, R., Markham, A., Groffen, J., Boguski, M S., Altschul, S F., Horii, A., Ando, H., Miyoshi, Y., Miki, Y., Nishisho, I., and Nakamura, Y. Identification of FAP locus genes from chromosome 5q21. Science (Washington D.C.) 253, 661–665 (1991).

Kuroki, T., Fujiwara, Y., Tsuchiya, E., Nakamori, S., Imaoka, S., Kanematsu, T., and Nakamura, Y. Accumulation of genetic changes during development and progression of hepatocellular carcinoma. Genes Chrom. Cancer 13, 163–167 (1995).

Lasko, Cavenee, and Nordenskjold, "Loss of Constitutional Heterozygosity in Human Cancer," Ann. Rev. Genetics, 25:281–314 (1991).

Latif F, Tory K, Gnarra J, Yao M, Duh F M, Orcutt M L, Stackhouse T, Kuzmin I, Modi W, Geil L, et al. Identification of the von Hippel-Lindau disease tumor suppressor gene. Science 260, 1317–1320 (1993).

Mao, L., Schoenberg, M P., Scicchitano, M., Erozan, Y S., Merlo, A., Schwab, D., and Sidranski, D. Molecular detection of primary bladder cancer by microsatellite analysis. Science (Washington D.C.) 271, 659–662 (1996).

Matteucci, et al., J. Am. Chem. Soc., 103:3185(1981)

Minna et al., 1989, Cancer Principals and Practices of Oncology, DeVita et al. ed. Lippincott, Philadelphia pp. 591–705

Miozzo, M., Sozzi, G., Musso, K., Pilotti, S., Incarbone, M., Pastorino, U., and Pierotti, M A. Microsatellite alterations in bronchial and sputum specimens of lung cancer patients. Cancer Res. 56, 2285–2288 (1996).

Nawroz, H., Koch, W., Anker, P., Stroun, M., and Sidransky, D. Microsatellite alterations in serum DNA of head and neck cancer patients. Nature Med 2, 1035–1037 (1996).

Rouleau G A, Merel P, Lutchman M, Sanson M, Zucman J, Marineau C, Hoang-Xuan K, Demczuk S, Desmaze C, Plougastel B, et al. Alteration in a new gene encoding a putative membrane-organizing protein causes neurofibromatosis type 2. Nature 363, 515–521 (1993).

Scharf (1986) Science 233: 1076.

Steck, P A., Pershouse, M A., Jasser, S A., Yung, W K A., Lin, H., Ligon, A H., Langford, L A., Baumgard, M L., Hattier, T., Davis, T., Frye, C., Hu, R., Swedlund, B., Teng, D H F., and Tavtigian. Identification of a candidate tumor suppressor gene, MMACI, at chromosome 10q23.3 that is mutated in multiple advanced cancers. Nat Genet. 15(4), 356–362 (1997).

Stroun, M., Anker, P., Lyautey, J., Lederrey, C., and Maurice, P A. Isolation and characterization of DNA from the plasma of cancer patients. Eur. J. Cancer Clin. Oncol. 23, 707–712 (1987).

Stroun, M., Anker, P., Maurice, P., Lyautey, J., Lederrey, C., and Beljanski, M. Neoplastic Characteristics of the DNA found in the plasma of cancer patients. Oncology 46, 318–322 (1989).

Vogelstein, B., Fearon, E R., Hamilton, S R., Kern, S E., Preisinger, A C., Leppert, M., Nakamura, Y., White, R., Smits, A M M., and Bos, J L. Genetic alterations during colorectal-tumor development. N. Engl. J. Med. 319, 525–532 (1988).

Wu, D. Y. et al. (1989). Genomics 4: 560–569.

What is claimed is:

1. A method of detecting melanoma in a patient comprising:
   a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
   b) detecting the presence or absence of the LOH marker; wherein the LOH of the marker is indicative of melanoma in the patient.

2. The method of claim 1 wherein the sample is acellular blood plasma.

3. The method of claim 1 wherein the LOH marker is a CA-repeat microsatellite marker.

4. The method of claim 1 wherein the LOH marker is from the D3S1293 locus.

5. The method of claim 1, wherein step a) further comprises amplifying nucleic acid from more than one of the LOH markers, and step b) further comprises detecting the presence or absence of more than one of the LOH markers.

6. The method of claim 5, wherein the LOH markers are from the D9S157 and D3S1293 loci.

7. The method of claim 5 wherein the LOH markers are D9S157 and D1S228.

8. The method of claim 5 wherein the LOU markers are from the D11S925 and D3S1293 loci.

9. The method of claim 1 wherein the LOH markers are detected with a primer labeled with a chromophore.

10. A method of monitoring treatment of melanoma in a patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
 b) detecting the presence or absence of the LOH marker; wherein the LOH of the marker is indicative of the efficacy of the treatment in the patient.

11. The method of claim 10 wherein the sample is acellular blood plasma.

12. The method of claim 10 wherein the LOH marker is a CA-repeat microsatellite.

13. The method of claim 10 wherein the LOH marker is from the D3S1293 locus.

14. The method of claim 10, wherein step a) further comprises amplifying nucleic acid from more than one of the LOH markers, and step b) further comprises detecting the presence or absence of more than one of the LOH markers.

15. The method of claim 14 wherein the LOH markers are from D9S157 and D3S1293 loci.

16. The method of claim 14 wherein the LOH markers are D9S157 and D1S228.

17. The method of claim 14 wherein the LOH markers are from the D11S925 and D3S1293 loci.

18. The method of claim 10 wherein the LOH markers are detected with a primer labeled with a chromophore.

19. A method of detecting subclinical melanoma in a patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
 b) detecting the presence or absence of the LOH marker; wherein the LOH of the marker is indicative of subclinical melanoma in the patient.

20. The method of claim 19 wherein the sample is acellular blood plasma.

21. The method of claim 19 wherein the LOH marker is a CA-repeat microsatellite marker.

22. The method of claim 19 wherein the LOH marker is from the D3S1293 locus.

23. The method of claim 19, wherein step a) further comprises amplifying nucleic acid from more than one of the LOH markers, and step b) further comprises detecting the presence or absence of more than one of the LOH markers.

24. The method of claim 23 wherein the LOH markers are from D9S157 and D3S1293 loci.

25. The method of claim 23 wherein the LOH markers are D9S157 and D1S228.

26. The method of claim 23 wherein the LOH markers are from the D11S925 and D3S1293 loci.

27. The method of claim 19 wherein the LOH markers are detected with a primer are labeled with a chromophore.

28. A method of prognosing melanoma in a melanoma patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
 b) detecting the presence or absence of the LOH marker; wherein an incease in the LOH of the marker is indicative of a poorer prognosis in the patient.

29. The method of claim 28 wherein the biological fluid is acellular blood plasma.

30. The method of claim 28 wherein the LOH marker is a CA-repeat microsatellite marker.

31. The method of claim 28 wherein the LOH marker is from the D3S1293 locus.

32. The method of claim 28, wherein step a) further comprises amplifying nucleic acid from more than one of the LOH markers, and step b) further comprises detecting the presence or absence of more than one LOH of the markers.

33. The method of claim 32 wherein the LOH markers are from the D9S157 and D3S1293 loci.

34. The method of claim 32 wherein the LOH markers are D9S157 and D1S228.

35. The method of claim 32 wherein the LOH markers are from the D1S925 and D3S1293 loci.

36. The method of claim 28 wherein the LOH markers are detected with a primer labeled with a chromophore.

37. A method of detecting melanoma in a patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
 b) detecting the presence or absence of two or more of the LOH markers; wherein the LOH of the markers is indicative of melanoma in the patient.

38. A method of monitoring treatment of melanoma in a patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S295; and
 b) detecting the presence or absence of two or more of the LOH markers; wherein the LOH of the markers is indicative of the efficacy of the treatment in the patient.

39. A method of detecting subclinical melanoma in a patient comprising:
 a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
 b) detecting the presence or absence of two or more of the LOH markers; wherein the LOH of the markers is indicative of subclinical melanoma in the patient.

40. A method of prognosing melanoma in a melanoma patient comprising:
   a) performing a nucleic acid amplification reaction in a sample derived from acellular blood plasma or serum from the patient, wherein the amplification reaction is designed to amplify a loss of heterozygosity (LOH) marker from a locus selected from the group consisting of D1S214, D1S228, D3S1293, D6S264, D9S157, D9S161, S10S212, D10S216, and D11S925; and
   b) detecting the presence or absence of two or more of the LOH markers; wherein an increase in the LOH of the markers is indicative of a poorer prognosis in the patient.

41. The method of claim 1 wherein the sample is serum.
42. The method of claim 1 wherein the LOH marker is from the D1S214 locus.
43. The method of claim 1 wherein the LOH marker is from the D1S228 locus.
44. The method of claim 1 wherein the LOH marker is from the D6S264 locus.
45. The method of claim 1 wherein the LOH marker is from the D9S157 locus.
46. The method of claim 1 wherein the LOH marker is from the D9S161 locus.
47. The method of claim 1 wherein the LOH marker is from the D10S212 locus.
48. The method of claim 1 wherein the LOH marker is from the D10S216 locus.
49. The method of claim 1 wherein the LOH marker is from the D11S925 locus.
50. The method of claim 10 wherein the sample is serum.
51. The method of claim 10 wherein the LOH marker is from the D1S214 locus.
52. The method of claim 10 wherein the LOH marker is from the D1S228 locus.
53. The method of claim 10 wherein the LOH marker is from the D6S264 locus.
54. The method of claim 10 wherein the LOH marker is from the D9S157 locus.
55. The method of claim 10 wherein the LOH marker is from the D9S161 locus.
56. The method of claim 10 wherein the LOH marker is from the D10S212 locus.
57. The method of claim 10 wherein the LOH marker is from the D10S216 locus.
58. The method of claim 10 wherein the LOH marker is from the D11S925 locus.
59. The method of claim 19 wherein the sample is serum.
60. The method of claim 19 wherein the LOH marker is from the D1S214 locus.
61. The method of claim 19 wherein the LOH marker is from the D1S228 locus.
62. The method of claim 19 wherein the LOH marker is from the D6S264 locus.
63. The method of claim 19 wherein the LOH marker is from the D9S157 locus.
64. The method of claim 19 wherein the LOH marker is from the D9S161 locus.
65. The method of claim 19 wherein the LOH marker is from the D10S212 locus.
66. The method of claim 19 wherein the LOH marker is from the D10S216 locus.
67. The method of claim 19 wherein the LOH marker is from the D11S925 locus.
68. The method of claim 28 wherein the sample is serum.
69. The method of claim 28 wherein the LOH marker is from the D1S214 locus.
70. The method of claim 28 wherein the LOH marker is from the D1S228 locus.
71. The method of claim 28 wherein the LOH marker is from the D6S264 locus.
72. The method of claim 28 wherein the LOH marker is from the D9S157 locus.
73. The method of claim 28 wherein the LOH marker is from the D9S161 locus.
74. The method of claim 28 wherein the LOH marker is from the D10S212 locus.
75. The method of claim 28 wherein the LOH marker is from the D10S216 locus.
76. The method of claim 28 wherein the LOH marker is from the D11S925 locus.
77. The method of claim 37 wherein the sample is acellular blood plasma.
78. The method of claim 37 wherein the sample is serum.
79. The method of claim 37 wherein one of the two markers is D3S1293.
80. The method of claim 37 wherein one of the two markers is D1S228.
81. The method of claim 37 wherein the LOH markers are from the D9S157 and D3S1293 loci.
82. The method of claim 37 wherein the LOH markers are D9S157 and D1S228.
83. The method of claim 37 wherein the LOH markers are from the D11S925 and D3S1293 loci.
84. The method of claim 37 wherein the LOH markers are detected with a primer labeled with a chromophore.
85. The method of claim 38 wherein the sample is acellular blood plasma.
86. The method of claim 38 wherein the sample is serum.
87. The method of claim 38 wherein one of the two markers is D3S1293.
88. The method of claim 38 wherein one of the two markers is D1S228.
89. The method of claim 38 wherein the LOH markers are from the D9S157 and D3S1293 loci.
90. The method of claim 38 wherein the LOH markers are D9S157 and D1S228.
91. The method of claim 38 wherein the LOH markers are from the D11S925 and D3S1293 loci.
92. The method of claim 38 wherein the LOH markers are detected with a primer labeled with a chromophore.
93. The method of claim 39 wherein the sample is acellular blood plasma.
94. The method of claim 39 wherein the sample is serum.
95. The method of claim 39 wherein one of the two markers is D3S1293.
96. The method of claim 39 wherein one of the two markers is D1S228.
97. The method of claim 39 wherein the LOH markers are from the D9S157 and D3S1293 loci.
98. The method of claim 39 wherein the LOH markers are D9S157 and D1S228.
99. The method of claim 39 wherein the LOH markers are from the D11S925 and D3S1293 loci.
100. The method of claim 39 wherein the LOH markers are detected with a primer labeled with a chromophore.
101. The method of claim 40 wherein the sample is acellular blood plasma.
102. The method of claim 40 wherein the sample is serum.
103. The method of claim 40 wherein one of the two markers is D3S1293.
104. The method of claim 40 wherein one of the two markers is D1S228.
105. The method of claim 40 wherein the LOH markers are from the D9S157 and D3S1293 loci.
106. The method of claim 40 wherein the LOH markers are D9S157 and D1S228.
107. The method of claim 40 wherein the LOH markers are from the D11S925 and D3S1293 loci.
108. The method of claim 40 wherein the LOH markers are detected with a primer labeled with a chromophore.

* * * * *